(12) United States Patent
Fujitani et al.

(10) Patent No.: US 9,993,209 B1
(45) Date of Patent: Jun. 12, 2018

(54) DYNAMICALLY MONITORING ENVIRONMENTAL AND PHYSIOLOGICAL CHARACTERISTICS TO GENERATE A MEDICINE INGESTION ALARM

(71) Applicant: International Business Machines Corporation, Armonk, NY (US)

(72) Inventors: Kanako Fujitani, Saitama-prefecture (JP); Mariko Ishige, Tokyo (JP); Yusuke Nishitani, Tokyo (JP); Yutaka Oishi, Kanagawa (JP); Tatsuya Sobue, Kanagawa-ken (JP); Masayuki Yamana, Kanagawa-ken (JP)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/494,813

(22) Filed: Apr. 24, 2017

(51) Int. Cl.
*A61B 5/00* (2006.01)
*A61B 5/11* (2006.01)
(Continued)

(52) U.S. Cl.
CPC ............ *A61B 5/746* (2013.01); *A61B 5/0002* (2013.01); *A61B 5/1112* (2013.01);
(Continued)

(58) Field of Classification Search
CPC ........ A61M 2205/50; A61M 2205/581; G06Q 50/22; G06Q 30/0623; G06F 19/3406;
(Continued)

(56) References Cited

U.S. PATENT DOCUMENTS

| 8,157,730 B2 | 4/2012 | LeBoeuf et al. |
| 8,810,392 B1 | 8/2014 | Teller et al. |

(Continued)

FOREIGN PATENT DOCUMENTS

| CN | 103607511 A | 2/2014 |
| CN | 102614084 A | 9/2015 |
| WO | 2008/083616 A1 | 7/2008 |

OTHER PUBLICATIONS

Lee et al., "Real-time Feedback for Improving Medication Taking", http://dl.acm.org/citation.cfm?id=2557210, CHI 2014, One of a CHInd, Session: Health and Everyday Life, 2014, pp. 2259-2268.

*Primary Examiner* — Orlando Bousono
(74) *Attorney, Agent, or Firm* — Ingrid M. Foerster; Edell, Shapiro & Finnan, LLC

(57) ABSTRACT

According to an embodiment of the present invention, a system dynamically monitors a patient's physiological condition and location information to generate an alarm signal to enable the patient to timely administer a health substance. Initially, the system monitors location information of a health substance and the patient and physiological information of the patient. A processor in the system determines a predicted time when the patient may attain a physiological condition for receiving the health substance and may further determine a transit time for the patient to travel to a location of the health substance. Based on the predicted and transit times, the system issues an alarm signal to the patient prior to the predicted time. Embodiments of the present invention further include a method and computer program product for monitoring a patient's physiological condition and location information to generate an alarm signal in substantially the same manner described above.

20 Claims, 9 Drawing Sheets

(51) Int. Cl.
*A61B 5/145* (2006.01)
*G08B 21/04* (2006.01)
*G06N 5/04* (2006.01)
*G06F 19/00* (2018.01)
*G06Q 30/06* (2012.01)

(52) U.S. Cl.
CPC ........ *A61B 5/14546* (2013.01); *A61B 5/4848* (2013.01); *A61B 5/7275* (2013.01); *G06F 19/3406* (2013.01); *G06N 5/04* (2013.01); *G06Q 30/0623* (2013.01); *G08B 21/0453* (2013.01); *A61B 2560/0242* (2013.01)

(58) Field of Classification Search
CPC .... G06N 5/04; G08B 21/0453; A61B 5/0002; A61B 5/0031; A61B 5/1112; A61B 5/14532; A61B 5/14546; A61B 5/4848; A61B 5/7275; A61B 5/746; A61B 2560/0242
See application file for complete search history.

(56) References Cited

U.S. PATENT DOCUMENTS

| | | | |
|---|---|---|---|
| 2010/0057057 A1* | 3/2010 | Hayter | A61B 5/14532 604/890.1 |
| 2010/0164716 A1 | 7/2010 | Estevez et al. | |
| 2010/0185456 A1 | 7/2010 | Kansal | |
| 2013/0214925 A1* | 8/2013 | Weiss | G08B 25/001 340/539.11 |
| 2013/0262138 A1* | 10/2013 | Jaskela | G06Q 50/22 705/2 |
| 2014/0316217 A1* | 10/2014 | Purdon | A61B 5/4821 600/301 |
| 2016/0140315 A1* | 5/2016 | Diaz | H04L 65/605 705/2 |
| 2016/0296697 A1* | 10/2016 | Hayter | A61B 5/14532 |
| 2016/0357924 A1* | 12/2016 | Jenkins | G06F 19/345 |
| 2017/0098058 A1* | 4/2017 | McCullough | A61M 5/14248 |
| 2017/0124285 A1* | 5/2017 | McCullough | A61M 5/14248 |

* cited by examiner

DYNAMICALLY MONITORING ENVIRONMENTAL AND PHYSIOLOGICAL CHARACTERISTICS TO GENERATE A MEDICINE INGESTION ALARM

BACKGROUND

1. Technical Field

Present invention embodiments relate to physiological monitoring systems, and more specifically, monitoring physiological characteristics of a patient and a distance between the patient and a health substance (e.g., medicine, dietary supplements, vitamins, injections, drugs, etc.) to dynamically generate an alarm signal for administering the health substance.

2. Discussion of the Related Art

As the use of medicines has increased, so too have the questions concerning the proper dosing times of the medicines, particularly if a patient is ingesting a cocktail of drugs. As differences are prevalent among individual patients with regard to the efficacy of their medicines, it may be difficult for an individual patient to accurately determine when to administer medicine. For example, even if the same dosage of the same medicine is administered to different patients, the therapeutic blood drug concentration among the different patients will differ depending on their physiological characteristics. Further complicating this issue is that home care patients often forget, or may not know, when to take their medicines or their blood concentration levels may rapidly change due to physiological disturbances. Consequently, a patient's blood drug concentration may unexpectedly fall, reducing the drug efficacy of the patient's medicine. The safety and welfare of the patient may therefore be compromised as the resistance of opportunistic bacteria and viruses within the patient may increase.

SUMMARY

According to an embodiment of the present invention, a system dynamically monitors a patient's physiological condition and location information to generate an alarm signal to enable the patient to timely administer one or more health substances. Initially, the system monitors location information of a health substance as well as the location information and physiological information of the patient. Based on the physiological information, a processor in the system may determine a predicted time when the patient may attain a physiological condition for receiving the health substance determining. The processor may further determine a transit time for the patient to travel to a location of the health substance based on the predicted time and the location information of the user and the health substance. Based on the predicted and transit times, the system may generate an alarm signal at a time to enable the patient to administer the health substance prior to the predicted time. Embodiments of the present invention further include a method and computer program product for dynamically monitoring a patient's physiological condition and location information to generate an alarm signal in substantially the same manner described above.

DETAILED DESCRIPTION

Present invention embodiments dynamically monitor a patient's physiological condition and location information to generate an alarm signal to enable the patient to timely administer one or more health substances. Initially, the system monitors location information of a health substance as well as the location information and physiological information of the patient. Based on the physiological information, a processor in the system may determine a predicted time when the patient may attain a physiological condition for receiving the health substance determining. The processor may further determine a transit time for the patient to travel to a location of the health substance based on the predicted time and the location information of the user and the health substance. Based on the predicted and transit times, the system may generate an alarm signal at a time to enable the patient to administer the health substance prior to the predicted time. Embodiments of the present invention further include a method and computer program product for capturing an image based on the context of the image in substantially the same manner as described above.

Present invention embodiments therefore utilize patient physiological and location information and location information associated with a health substance to dynamically generate an alarm signal notifying the patient when to travel to the location of the health substance. For example, physiological information of a patient is dynamically monitored and analyzed to predict a time when the blood concentration level of the health substance will fall below an efficacious level within the patient. Depending on the predicted time, and a transit time needed for the patient to reach the location of the health substance, a time is determined when an alarm should be generated to allow the patient to reach the health substance before the blood concentration level in the patient becomes ineffective. The disclosed embodiments may therefore monitor a patient's physiological and location information to generate an alarm signal notifying a patient to travel to the location of a health substance, making it easier for the patient to ensure the proper administration of the health substance, regardless of the subjective physiological characteristics of the user and/or the location of the health substance.

Figure 1:
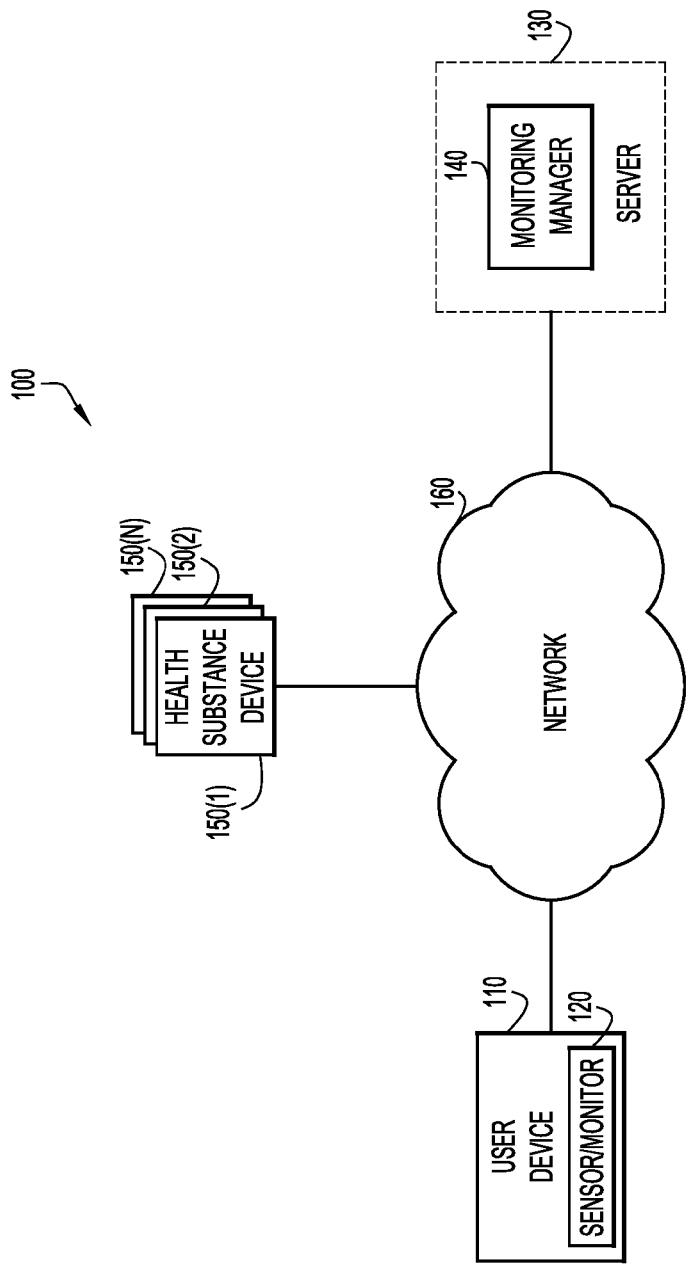
FIG. 1 is a diagrammatic illustration of an example computing environment for use with an embodiment of the present invention.

An example computing environment for use with present invention embodiments is illustrated in FIG. 1. Specifically, environment 100 includes a user device 110, one or more servers 130, and one or more health substance devices 150. Server 130 may comprise one or more monitoring managers 140, which are responsible for monitoring physiological and location information associated with a patient connected to user device 110 as well as location information received from one or more health substance devices 150. Server 130 and user device 110 may be remote from each other and communicate over a network 160. Network 160 may be implemented by any number of any suitable communications media (e.g., wide area network (WAN), local area network (LAN), Internet, Intranet, etc.). Alternatively, server 130 and user device 110 may be local to each other, and communicate via any appropriate local communication medium (e.g., local area network (LAN), hardwire, wireless link, Intranet, etc.).

User device 110 may comprise one or more sensor/monitors 120 that enable a patient connected to user device 110 to measure one or more physiological characteristics associated with the patient. User device 110 may forward information related to the one or more physiological characteristics to server 130, and, in response, may receive one or more alert times from server 130. For example, user device 110 may receive an alert time from server 130 indicating when user device 120 should generate an alarm to notify a patient to travel to the location of a health substance.

Initially, server 130 receives, from user device 110, one or more physiological characteristics and location information associated with a patient connected to user device 110. After receiving the physiological and location information, monitoring manager in server 130 may determine a predicted time when the blood drug concentration level of one or more health substances in the patient will fall below an efficacious level. Server 130 may further receive, from one or more health substance devices 150, location information associated with one or more health substances. Based on location information associated with the patient and the one or more health substances, server 130 may determine a transit time when the patient should leave to reach the one or more health substances before the one or more health substances becomes ineffective. Accordingly, server 130 may send one or more alert times to user device 110 indicating when user device 110 should generate one or more alarms notifying a patient when to travel to reach the one or more health substances.

Figure 2:
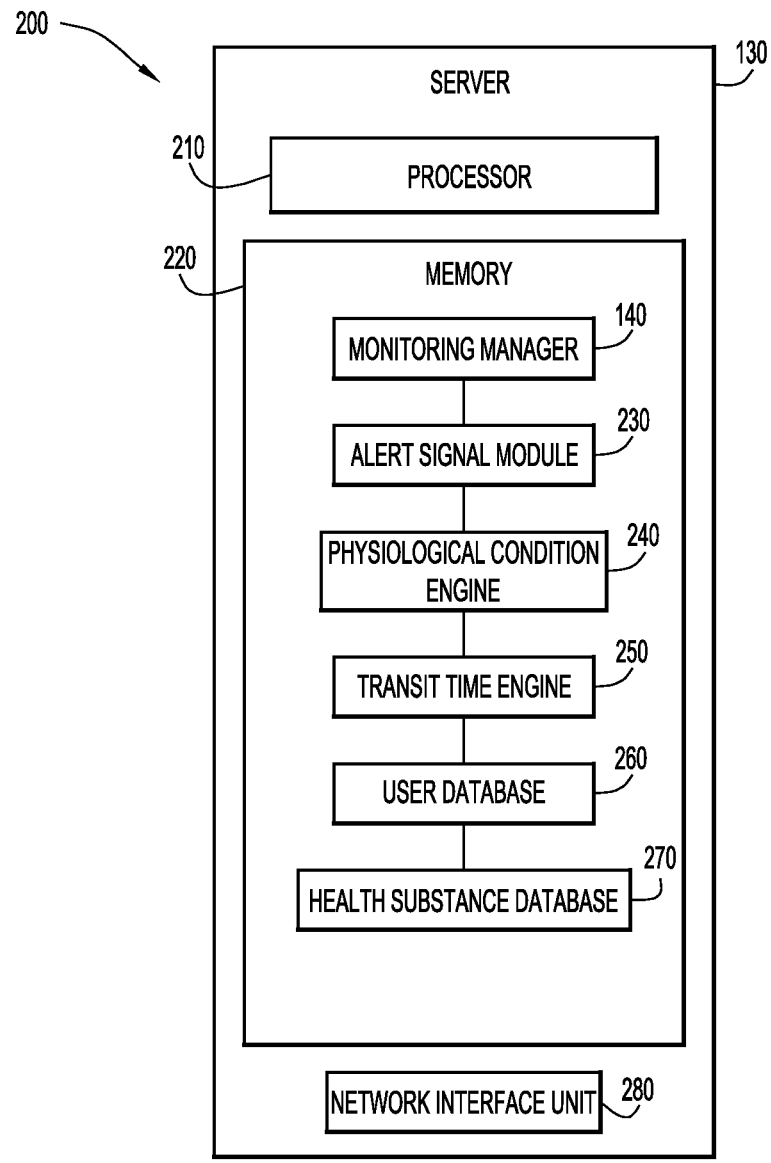
FIG. 2 is a block diagram illustrating a server of FIG. 1 in more detail according to an embodiment of the present invention.

Reference is now made to FIG. 2, which shows an example block diagram of server 130 configured to perform message processing according to present invention embodiments. It should be understood that there are numerous possible configurations for server 130 and FIG. 2 is meant to be an example of one of the possible configurations. Server 130 includes a processor 210, memory 220 and a network interface unit 280. The network interface (I/F) unit (NIU) 280 is, for example, an Ethernet card or other interface device that allows server 130 to communicate over communication network 160. Network I/F unit 280 may include wired and/or wireless connection capabilities.

Processor 210 may include a collection of microcontrollers and/or microprocessors, for example, each configured to execute respective software instructions stored in the memory 220. Portions of memory 220 (and the instruction therein) may be integrated with processor 210.

Memory 220 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, memory 220 may comprise one or more computer readable storage media (e.g., a memory device) encoded with software comprising computer executable instructions and when the software is executed (e.g., by processor 210) it is operable to perform the operations described herein. For example, memory 220 stores or is encoded with instructions or modules for monitoring manager 140, which is configured to analyze incoming physiological and location information associated with a patient and location information associated with one or more health substances to determine when user device 110 should generate an alarm signal to notify the patient to travel to the location of the one or more health substances. Optionally, user device 110 and/or server 130 may, individually or in combination, include monitoring manager 140 to perform the monitoring of physiological and location information to generate an alarm signal to notify a patient when to travel to one or more health substances.

Accordingly, memory 220 may store or is encoded with instructions for monitoring manager 230 to perform overall control of the monitoring operations described herein by receiving physiological and location information from user device 110 and location information from one or more health substance devices 150 and generating one or more alert times based on the physiological and location information. Monitoring manager 230 is further configured to store the received physiological, environmental and location information associated with one or more patients in patient database 260 and location information associated with one or more health substances in health substance database 270 for further monitoring operations. According to an embodiment of the present invention, monitoring manager 140 may further send to user device 110 an indication of a location of one or more health substances that is closest to a patient connected to user device 110.

Memory 220 may further store or is encoded with instructions for alert signal module 230, physiological condition engine 240, transit time engine 250, patient database 260 and health substance database 270. Alert signal module 240 is further configured to determine one or more alert signals based on received physiological and location information and to send the one or more alert signals to user device 110.

Physiological condition engine 240 may analyze received physiological characteristics associated with one or more patients to determine one or more physiological conditions or states associated with the one or more patients. For example, based on received physiological information associated with a patient, physiological condition engine 240 may estimate a prediction time when a blood drug concentration level of a health substance will reach an ineffective level within the patient. Physiological condition engine 240 may further determine a rate at which a patient retains and/or dissolves a health substance based on physiological and environmental characteristics associated with the patient.

Based on one or more prediction times associated with one or more patients, transit time engine 250 may use location information associated with the one or more patients and one or more health substances to determine when the one or more patients should go to the location of the one or more health substances to avoid reaching a physiological condition wherein the one or more health substances are no longer effective within the one or more patients. For example, if physiological condition engine 240 determines that a concentration of a health substance will become ineffective within a patient in two hours and transmit time engine 250 determines that the patient is currently thirty minutes from a nearest location of the health care substance, transit time engine 250 will determine that the patient should leave to travel to the health substance in 1.5 hours. Accordingly, server 130 may send an alert time to user device 110 indicating that user device 110 should generate an alarm in 1.5 hours to notify the patient to leave to go to the nearest location of the health substance. According to an embodiment of the present invention, transit time engine 250 may determine one or more locations associated with one or more health substances by receiving inventory information from one or more health substance repositories, e.g., hospitals, pharmacies, doctors' offices, etc. According to a further embodiment of the present invention, transit time engine 250 may determine a location associated with one or more health substances nearest to a patient by analyzing data received from one or more mapping tools and/or search engines (e.g., Google Maps, Maps.com, Yahoo! Maps, etc.).

Monitoring manager 140, alert signal module 230, physiological condition engine 240, and transit time engine 250 may include one or more modules or units to perform the various functions of present invention embodiments described below. The various modules (e.g., monitoring manager, alert signal module, physiological condition engine, transit time engine, etc.) may be implemented by any combination of any quantity of software and/or hardware modules or units, and may reside within memory 220 of server 130 for execution by processor 210.

Memory 220 may further provide patient database 260, which stores various information used and received by monitoring manager 230 for dynamic monitoring associated with a patient connected to user device 110. For example, patient database 260 may store one or more physiological and environmental characteristics associated with a patient (e.g., blood drug concentration levels, patient temperature, ambient temperature, blood pressure, rate at which the patient retains the health substance in the blood, etc.), and/or one or more parameters associated with device 110 (e.g., registration ID, patient ID, encryption keys, session keys, etc.). Patient database 260 may be implemented by any conventional or other database or storage unit, may be local to or remote from server 130, and may communicate via any appropriate communication medium (e.g., local area network (LAN), wide area network (WAN), Internet, hardwire, wireless link, Intranet, etc.).

Memory 220 may further provide health substance database 270, which stores various information used and received by monitoring manager 230 associated with one or more health substances. For example, health substance database 270 may store location information associated with one or more health substances (e.g., hospitals, pharmacies, doctors' offices), which may be utilized by transit time engine 250 to determine a nearest location of one or more health substances to one or more patients. Health substance database 270 may be implemented by any conventional or other database or storage unit, may be local to or remote from server 130, and may communicate via any appropriate communication medium (e.g., local area network (LAN), wide area network (WAN), Internet, hardwire, wireless link, Intranet, etc.).

Server 130 may be implemented by any conventional or other computer systems preferably equipped with a display or monitor, a base (e.g., including at least one processor 210, one or more memories 220 and/or internal or external network interfaces or communications devices 280 (e.g., modem, network cards, etc.), optional input devices (e.g., a keyboard, mouse or other input device), and any commercially available and custom software (e.g., server/communications software, activity context processor module, etc.).

Figure 3:
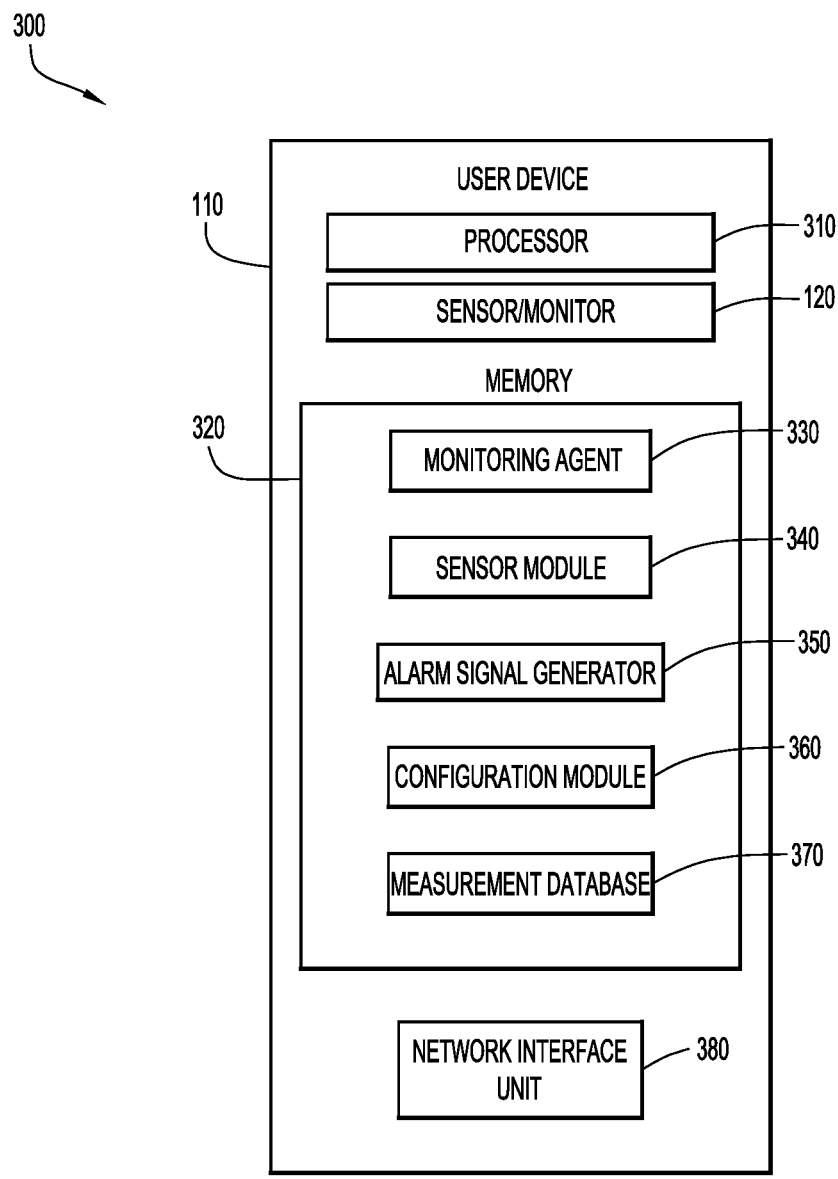
FIG. 3 is a block diagram illustrating a user device of FIG. 1 in more detail according to an embodiment of the present invention.

Reference is now made to FIG. 3, which shows an example block diagram of a user device 110 configured to monitor one or more physiological and/or environmental characteristics associated with a patient connected to user device 110 and to receive one or more alert times from server 130 indicating when user device 110 should generate one or more alarm signals notifying a patient when to travel to one or more locations associated with one or more health substances according to present invention embodiments. It should be understood that there are numerous possible configurations for user device 110 and FIG. 3 is meant to be an example of one of the possible configurations. User device 110 includes a processor 310, sensor/monitor 120, memory 320 and a network interface unit 380. The network interface (I/F) unit (NIU) 380 is, for example, an Ethernet card or other interface device that allows image capture device 110 to communicate over communication network 160. Network I/F unit 380 may include wired and/or wireless connection capabilities.

Processor 310 may include a collection of microcontrollers and/or microprocessors, for example, each configured to execute respective software instructions stored in the memory 320. Memory 320 may include various modules for execution by processor 310, including monitoring agent 330, sensor module 340, alarm signal generator 350, patient configuration module 360, and measurement database 370. Portions of memory 320 (and the instructions or modules therein) may be integrated with processor 310.

Sensor/monitor 120 may comprise one or more physiological and/or environmental sensors that enable user device 110 to measure one or more physiological attributes and/or one or more environmental parameters associated with a patient connected to user device 110 (e.g., blood pressure, heart rate, blood drug concentration levels, body temperature, ambient temperatures, patient location, etc.). For example, sensor/monitor 120 may include any sensor capable of measuring one or more physiological attributes and/or one or more environmental parameters (e.g., health substance monitors, blood sensors, thermometers, etc.). According to an embodiment of a present invention, sensor/monitor 120 may include sensors that are located internally in a patient and periodically send one or more measurements to user device 110, which may be worn externally to the patient (e.g., belt, backpack, etc.).

Memory 320 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, memory 320 may comprise one or more computer readable storage media (e.g., a memory device) encoded with software comprising computer executable instructions and when the software is executed (e.g., by processor 310) it is operable to perform the operations described herein. For example, memory 320 stores or is encoded with instructions for monitoring agent 330 to perform overall control of the receiving and displaying operations of dynamically monitoring one or more physiological and/or environmental characteristics associated with a patient, including sensor module 340, alarm signal generator 350, patient configuration module 360, and patient measurement database 370. Monitoring agent 330 is further configured to send one or more user physiological and/or environmental parameters to monitoring manager 130 to determine, based on the received parameters and/or location information, when to notify a patient to move to the location of one or more health substances.

Sensor module 340 is configured to detect and/or identify one or more physiological and/or one or more environmental parameters associated with a patient and/or user device 110 (e.g., body temperature, blood drug concentration level, amount of patient movement, ambient temperature, location, etc.). For example, sensor module 340 may determine, e.g., via sensor/monitor 120, a blood drug concentration level of one or more health substances within a patient and/or a body temperature of the patient. Similarly, sensor module may determine, using Global Positioning Service (GPS), the location of the patient connected to user device 110, and may also determine the ambient temperature near or around user device 110.

Alarm signal generator 350 is configured to generate, in response to receiving one or more alert times from server 130, one or more alarm signals to notify a patient connected to user device 110 to travel to one or more health substances. For example, alarm signal generator 350 may generate an alarm signal to notify a patient connected to user device 110 to drive to a local pharmacy to purchase a health substance (e.g., vitamins, medicine, drugs, etc.). It should be understood that the one or more alarm signals may be any indicator or sound (e.g., ringing, ring tone, buzzing, flashing lights, etc.) capable of alerting a patient connected to user device 110 to travel to a location of one or more health substances.

According to an embodiment of the present invention, alarm signal generator 350 is further configured to display on user device 110 one or more locations where one or more health substances are stored and/or sold. For example, alarm signal generator may generate a display informing a patient that the nearest location of blood pressure medicine is a pharmacy located approximately two miles from the patient's current location.

Patient configuration module 360 is configured to allow a patient to set one or more parameters and/or preferences associated with sensor/monitor 120 and related to notification generation by alarm signal generator 350. Patient configuration module 360 may allow a patient to specify one or more physiological and/or environmental characteristics and/or parameters to be measured by monitor/sensor 120 as well as the frequency at which monitor/sensor should measure the one or more physiological and/or environmental characteristics and/or parameters (e.g., every 30 minutes, every hour, every 6 hours, etc.). Patient configuration module 360 may be further configured to allow a patient to select a type of alarm generated by alarm signal generator (e.g., ring tone, ringing bell, music, etc.). According to an embodiment of the present invention, patient configuration module 360 may be further configured to allow a patient to configure display information generated by alarm signal generator 350. For example, a patient may configure alarm signal generator 350 to display the closest five locations of a health substance relative to a current position associated with the patient.

Monitoring agent 330, sensor module 340, alarm signal generator 350, and patient configuration module 360 may include one or more modules or units to perform the various functions of present invention embodiments described below. The various modules (e.g., monitoring agent, sensor module, alarm signal generator, patient configuration module, etc.) may be implemented by any combination of any quantity of software and/or hardware modules or units, and may reside within memory 320 of user device 110 for execution by processor 310.

Memory 320 may further provide patient measurement database 370, which stores various information used and generated by the various modules (e.g., monitoring agent, sensor module, alarm signal generator, patient configuration module, etc.) for monitoring one or more physiological and/or environmental parameters and/or characteristics associated with a patient connected to user device 110. For example, patient measurement database 370 may store one or more characteristics or preferences associated with a patient (e.g., blood pressure, heart rate, blood drug concentration levels, amount of movement, body temperature, patient location), and/or one or more environmental parameters associated with device 110 (e.g., ambient temperature, time of day, date, etc.). Patient measurement database 370 may be implemented by any conventional or other database or storage unit, may be local to or remote from server 130, and may communicate via any appropriate communication medium (e.g., local area network (LAN), wide area network (WAN), Internet, hardwire, wireless link, Intranet, etc.).

Figure 4:
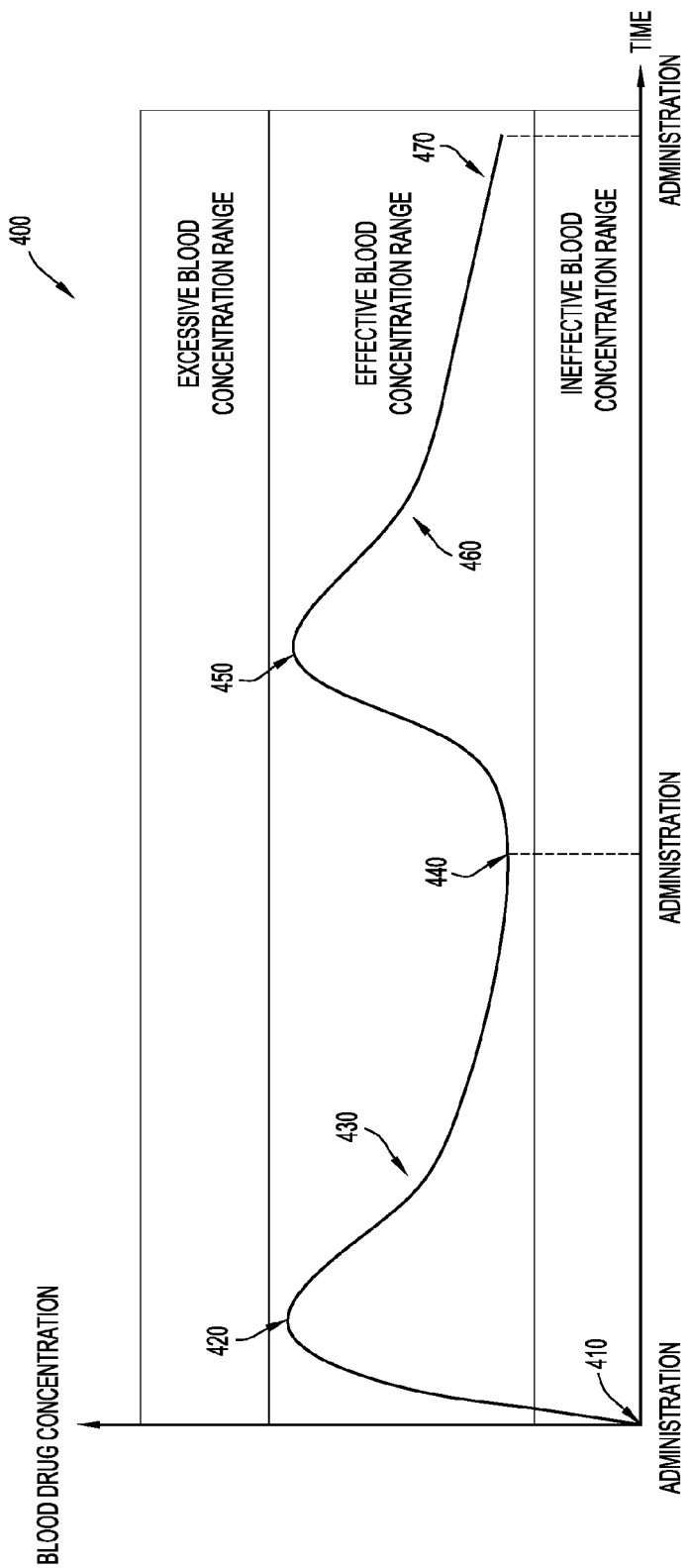
FIG. 4 is a diagrammatic illustration of an example manner in which a blood drug concentration level of a health substance is maintained over time according to an embodiment of the present invention.

A diagrammatic illustration of a process 400 in which a blood drug concentration level of a health substance is maintained over time according to an embodiment of the present invention is shown in FIG. 4.

By way of example, a patient's blood drug concentration level may include three distinct ranges: an ineffective blood concentration range, an effective blood concentration range, and excessive blood concentration range. For example, if a blood drug concentration level of a health substance in a patient is within an ineffective blood concentration range, the health substance is likely not efficacious to the patient. Similarly, if a blood drug concentration level of a health substance in a patient is within an effective blood concentration range, the concentration of the health substance within the patient is likely to be both safe and efficacious. Finally, if a blood drug concentration level of a health substance in a patient is in an excessive blood concentration range, the concentration of the health substance within the patient is likely unsafe, placing the patient at risk for adverse side-effects (e.g., cramping, vomiting, dizziness, etc.) and/or possibly death.

Initially, a health substance is administered to a patient at step 410. As illustrated in FIG. 4, if a proper dosage of the health substance is administered to the patient, the blood drug concentration level of the health substance within the patient may quickly rise to a peak in the effective blood concentration range at step 420.

The blood drug concentration level of the health substance may decay after peaking at step 430. According to an embodiment of the present invention, the rate at which the blood drug concentration level may decay may be dependent on various physiological and/or environmental characteristics, including the ease with which the patient maintains a health substance in the bloodstream and/or the rate at which the health substance wears off within the patient.

The health substance may be re-administered when the blood drug concentration level of the health substance nears the ineffective blood concentration range at step 440. As before, the blood drug concentration level of the health substance within the patient may quickly rise to a peak in the effective blood concentration range at step 450.

The blood drug concentration level of the health substance again may decay after peaking at step 460. The health substance then may be re-administered when the blood drug concentration level of the health substance nears the ineffective blood concentration range at step 470, and process 400 ends.

Figure 5:
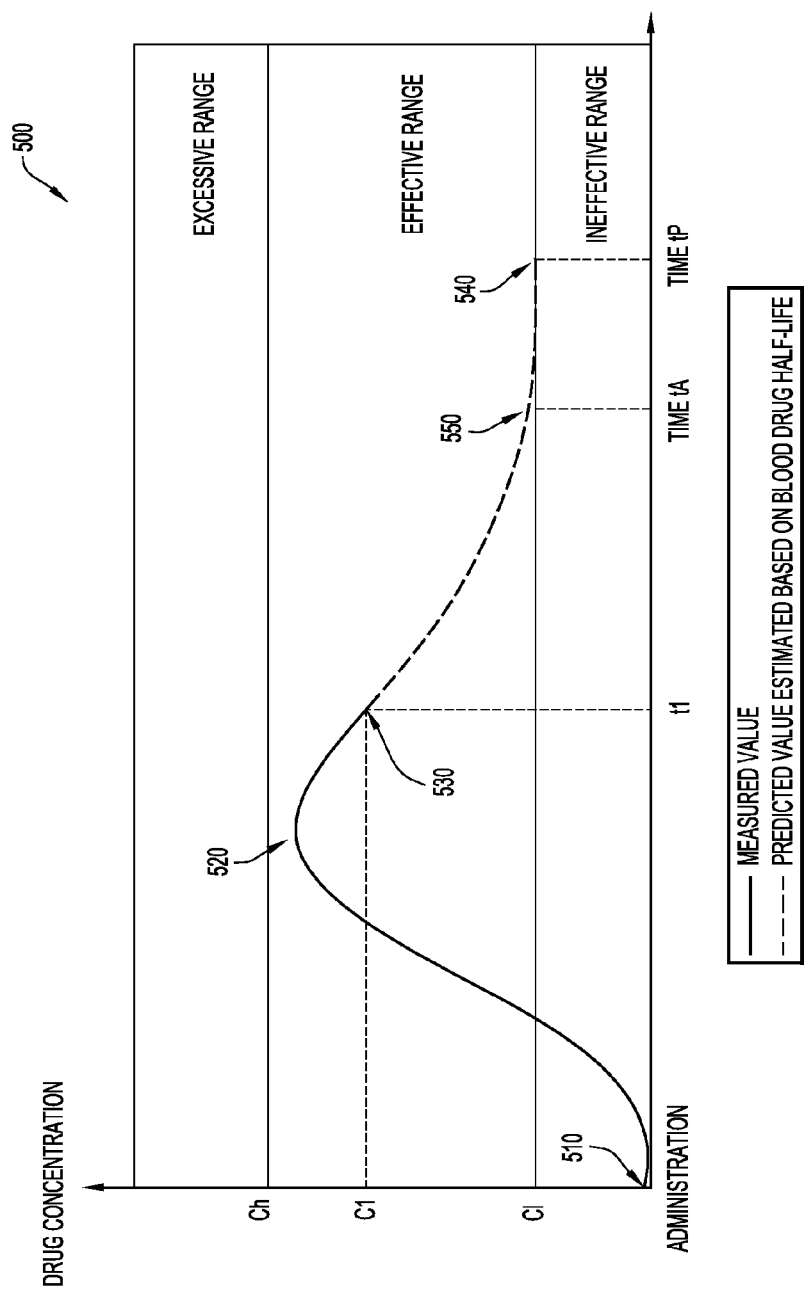
FIG. 5 is a diagrammatic illustration of an example manner in which a predicted time is estimated at which the efficacy of a health substance in a patient will become ineffective according to an embodiment of the present invention.

A diagrammatic illustration of a process 500 in which a predicted time is estimated at which the efficacy of a health substance in a patient will become ineffective according to an embodiment of the present invention is shown in FIG. 5.

Initially, a health substance is administered to a patient at step 510. A blood drug concentration level of the health substance within the patient is measured and a peak concentration level is detected at step 520.

At time t1, the blood drug concentration level of the health substance is measured to be at a level of C1 at step 530.

Based on the known half-life of the health substance, a time tP at which the blood drug concentration level will fall below the effective range is estimated at step 540. According to an embodiment of the present invention, time tP may be determined from the following equation:

$$C1=C1*(0.5)^{(tp-t1)/(T+\Delta T)} \quad \text{[Equation 1]}$$

$\Delta T$ is a physiological paramater associated with the patient and indicates the ease with which the patient retains medicine in the blood. Accordingly, $\Delta T$ is taken as a correction term that takes into account differences among individuals with respect to the ease with which a health substance remains efficacious within the patient.

Based on physiological and environmental parameters and/or characteristics associated with the patient, a time tA at which the blood drug concentration level within the patient will decrease to a concentration that is outside the effective range is estimated at step 550, and process 500 ends.

According to an embodiment of the present invention, time tA may be determined from tP using the following equation:

$$tA=tp+\Delta t(H,E) \quad \text{[Equation 2]}$$

$\Delta t(H, E)$ is a correction term that takes into account the rate at which the efficacy of a health substance decays in a particular patient based on physiological information vector H and environmental information vector E associated with the patient. For example, physiological information vector H may include one or more physiological parameters associated with the patient (e.g., amount of movement, body temperature, heart rate, etc.) and environmental information vector E may include one or more environmental parameters associated with the patient (e.g., air temperature, air pressure, location, etc.). According to a further embodiment of the present invention, physiological information vector H, environmental information vector E, and the value of the correction term $\Delta t(H, E)$ may be initially estimated and/or updated through a training process executed before process 500 is executed.

Figure 6:
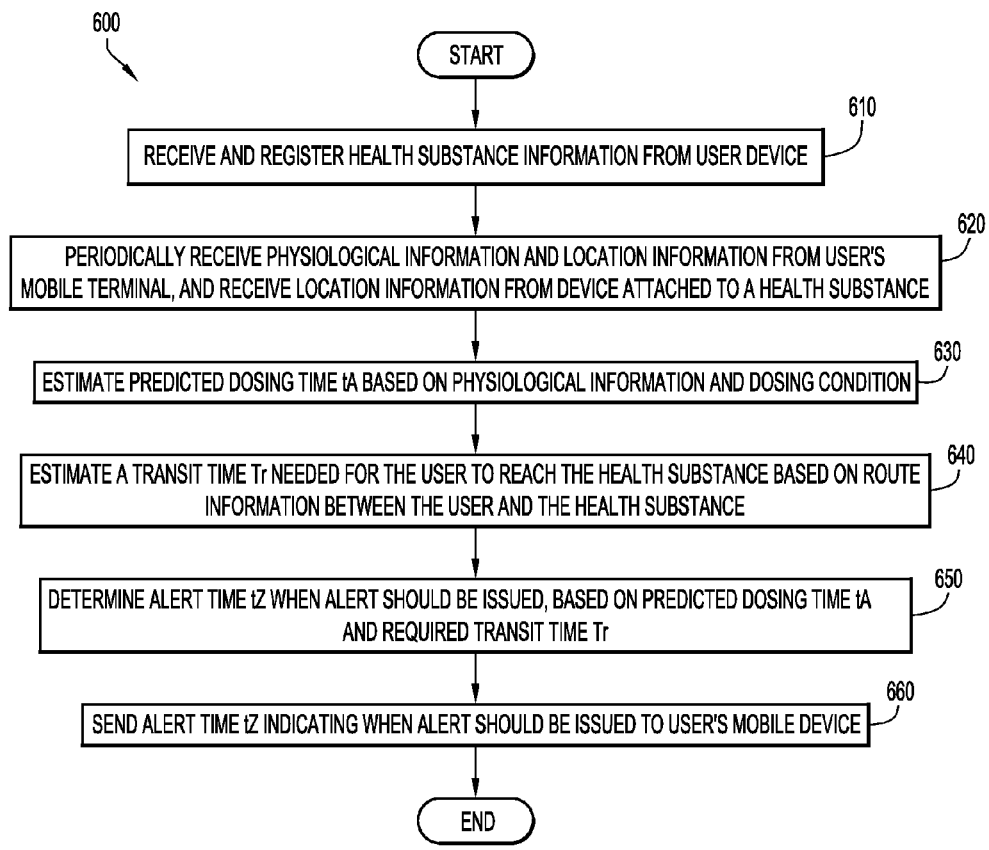
FIG. 6 is a procedural flow chart illustrating a manner of monitoring physiological and environmental characteristics to generate an alarm signal according to an embodiment of the present invention.

With reference to FIG. 6, there is depicted a procedural flow chart illustrating a method 600 in which physiological and environmental characteristics are dynamically monitored to generate an alarm signal according to an embodiment of the present invention. Method 600 is performed primarily by monitoring manager 140.

In accordance with process 600, patient configuration module 260 may be preconfigured with one or more security parameters and/or user preferences associated with a patient connected to user device 110 and/or one or more environmental parameters associated with user device 110.

Initially, server 130 may receive and register health substance information from user device 110 (e.g., mobile device, laptop, desktop, etc.) at step 610

Thereafter, server 130 may periodically receive physiological information and location information from user device 110, and location information of one or more health substances from one or more health substance devices 150 at step 620.

Server 130 may calculate a predicted dosing time A for the one or more health substances based on the physiological information associated with the patient. For example, based the physiological information associated with the patient, physiological condition engine 240 may determine a time tA at which the blood drug concentration level within the patient will decrease to a concentration that is outside the effective range.

Server 130 may calculate a transit time Tr needed for the patient to reach the health substance based on route information between patient and health substance at step 640. For example, using data received from one or more mapping tools and/or search engines (e.g., Google Maps, Maps.com, Yahoo! Maps, etc.), transit time engine 250 may estimate the amount of time needed for the patient to reach the closest location of the one or more health substances.

Server 130 may then determine an alert time Z at which an alert should be issued, based on predicted dosing time tA and transit time Tr at step 650. For example, alert signal module 230 may determine an alert time Z at which user device 110 should notify a patient to travel to a location associated with one or more health substances by subtracting the required transit time Tr from the predicted dosing time tA.

Server 130 may send the alert time Z to user device 110 at step 660, and process 600 ends.

Figure 7:
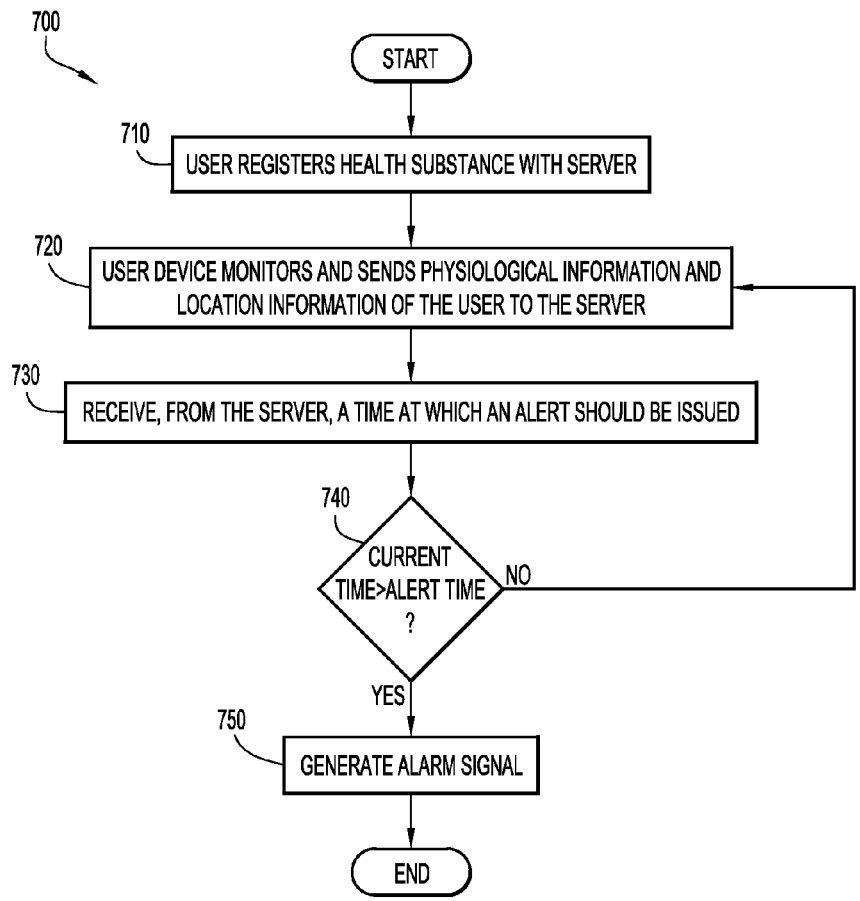
FIG. 7 is a procedural flow chart illustrating a manner of generating an alarm according to an embodiment of the present invention.

With reference to FIG. 7, there is depicted a procedural flow chart illustrating a method 700 in which alarm signal is generated according to an embodiment of the present invention. Method 700 is performed primarily by monitoring agent 330.

In accordance with method 700, patient configuration module 360 may be preconfigured with one or more security parameters and/or user preferences associated with a patient connected to user device 110 and/or one or more environmental parameters associated with user device 110.

Initially, a patient connected to user device 110 may register one or more health substances with server 130 at step 710.

User device 110 may monitor physiological information and location information of the patient related to the one or more health substances and sends the physiological information and location information to server 130 at step 720.

User device 110 may receive, from server 130, an alert time indicating when user device 110 should generate an alarm signal to notify a patient to travel to a location associated with the one or more health substances at step 730.

Alarm signal generator 350 determines whether the current time is greater than the alert time at step 740. If the current time is less than the alert time, user device 110 continues to monitor and send physiological and location information associated with the patient to server 130.

If the current time is greater than the alert time, alarm signal generator 350 issues an alarm signal at step 750, and process 700 ends.

Figure 8:
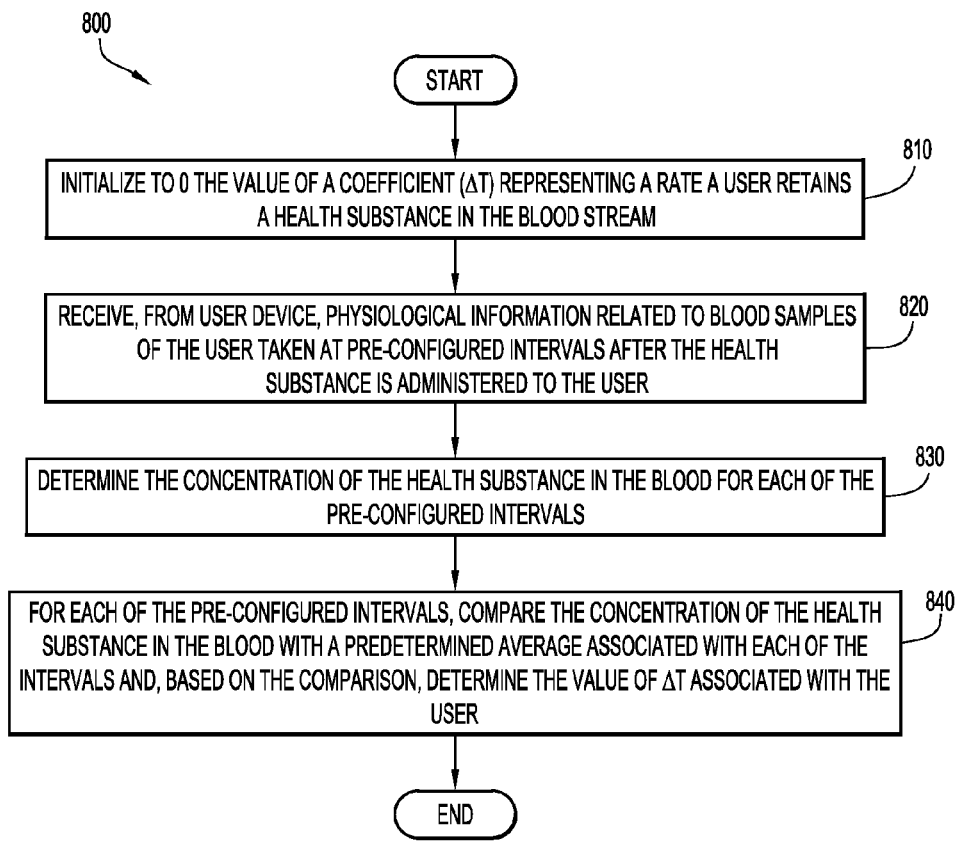
FIG. 8 is a procedural flow chart illustrating a manner of determining a rate a patient retains a health substance in the blood stream is determined according to an embodiment of the present invention.

With reference to FIG. 8, there is depicted a procedural flow chart illustrating a method 800 of determining a rate a patient retains a health substance in the blood stream according to an embodiment of the present invention. Method 800 is performed primarily by monitoring manager 140.

Initially, server 130 may set to 0 the value of a coefficient (ΔT) representing a rate a patient retains a health substance in the blood stream at step 810.

Server 130 receives, from user device 110, physiological information related to blood samples of the patient taken at pre-configured intervals after the health substance is administered to the patient at step 820, and may determine the concentration of the health substance in the blood for each of the pre-configured intervals at step 830.

For each of the pre-configured intervals, physiological condition engine 240 may compare the concentration of the medicine in the blood with a predetermined average associated with each of the intervals and, based on the comparison, determine the value of ΔT associated with the patient at step 840, and process 800 ends. According to an embodiment of the present invention, if the value of the coefficient ΔT is dependent on one or more physiological characteristics associated with the patient (e.g., gender, weight, height, age, etc.), the value of ΔT may be initially set to be equal to an average of ΔT that is associated with the one or more physiological characteristics.

Figure 9:
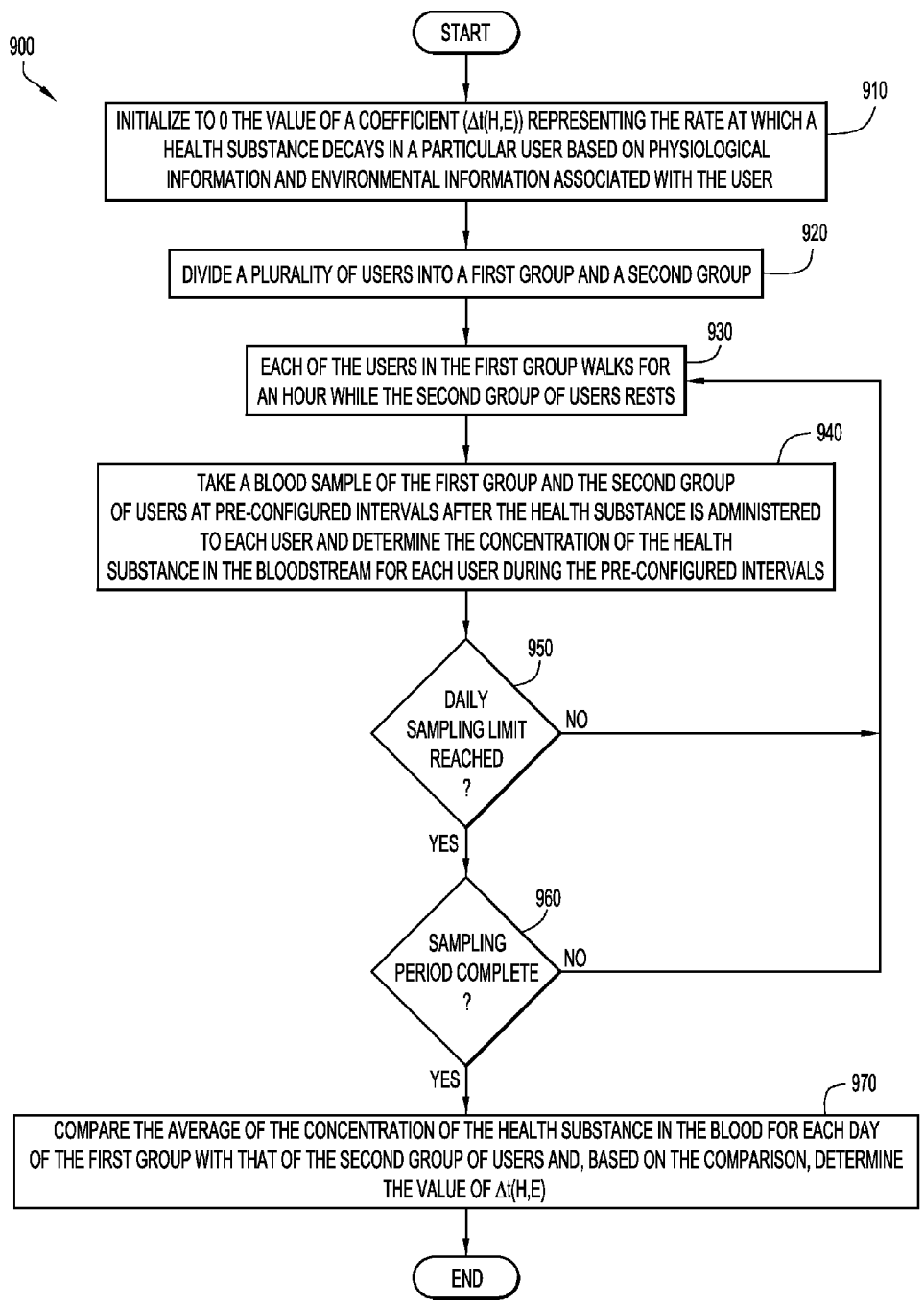
FIG. 9 is a procedural flow chart illustrating a manner of determining a rate of health substance efficacy based on physiological and environmental characteristics according to an embodiment of the present invention.

With reference to FIG. 9, there is depicted a procedural flow chart illustrating a method 900 of determining a rate of health substance efficacy based on physiological and environmental characteristics according to an embodiment of the present invention.

At step 910, server 130 may initialize to 0 the value of a coefficient (Δt(H,E)) representing the rate at which a health substance decays in a particular patient based on physiological information and environmental information associated with the patient at step 910.

At step 920, a plurality of patients may be divided into a first group of patients and a second group of patients.

At 930, the first group of patients may walk for an hour while the second group of patients may rest.

At step 940, a blood sample of each patient in the first group and the second group of patients is taken at pre-configured intervals after the health substance is administered to each patient and physiological engine 240 may determine the concentration of the health substance in the bloodstream for each patient during the pre-configured intervals. According to an embodiment of the present invention, monitoring manager 140 may store the blood sample information and health substance concentration levels of each patient in memory 220, e.g., patient database 260.

At step 950, a determination is made as to whether the limit of daily sampling was reached. If it is determined that the limit of daily sampling was not reached, the first group of patients may walk for another thirty minutes, after which blood samples of each patient in the first and second group are retaken and the concentration levels of the health substance for each of the patients are again determined.

At step 960, if it is determined that the limit of daily sampling was reached, a determination is made as to whether the sampling period is complete. If it is determined that the sampling period is not complete, the first group of patients may walk for another thirty minutes, after which blood samples of each patient in the first and second group are retaken and the concentration levels of the health substance for each of the patients is again determined.

At step 970, if it is determined that the sampling period is complete, physiological engine 240 compares the average concentration of the health substance in the bloodstream each day for each patient in the first group to that of each patient in the second group and, based on the comparison, determines the value of Δt(H,E), and process 900 ends.

Advantages of the present invention embodiments include real-time monitoring of one or more physiological and environmental characteristics associated with a patient and location information of one or more health substances associated with the patient. Based on the real-time monitoring, the system may generate an alarm signal to enable a patient to travel to and administer the one or more health substances before the efficacy of the one or more health substances wears off. The system may further dynamically determine a nearest location of the one or more health substances associated with a patient and may display to the patient an address and/or directions associated with one or more locations of the one or more health substances.

It will be appreciated that the embodiments described above and illustrated in the drawings represent only a few of the many ways of implementing embodiments for dynamically monitoring environmental and physiological characteristics to generate a medicine ingestion alarm.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.).

The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., message notification manager, sentiment analyzer, environment evaluator module, context analyzer, modification engine, etc.). These systems may include any types of monitors and input devices (e.g., keyboard, mouse, voice recognition, etc.) to enter and/or view information.

It is to be understood that the software (e.g., monitoring manager, alert signal module, physiological condition engine, transit time engine, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g. monitoring manager, alert signal module, physiological condition engine, transit time engine, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store messages, message-related data, user preferences and/or characteristics and one or more environmental parameters (e.g., user device configuration settings, public/private location, network attributes, etc.). The database system may be implemented by any number of any conventional or other databases, data stores or storage structures (e.g., files, databases, data structures, data or other repositories, etc.) to store information (e.g., user device configuration settings, public/private location, network attributes, etc.). The database system may be included within or coupled to the server and/or client systems. The database systems and/or storage structures may be remote from or local to the computer or other processing systems, and may store any desired data (e.g., user device configuration settings, public/private location, network attributes, etc.).

The present invention embodiments may employ any number of any type of user interface (e.g., Graphical User Interface (GUI), command-line, prompt, etc.) for obtaining or providing information (e.g., messages, analytics, configurations, user or other preferences, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion. The report may include any information arranged in any fashion, and may be configurable based on rules or other criteria to provide desired information to a user (e.g., user device configuration settings, public/private location, network attributes, etc.).

The present invention embodiments are not limited to the specific tasks or algorithms described above, but may be utilized for any type of health substance (e.g., medicine, vitamins, drugs, etc.) to perform any type of alarm signal generation (e.g., ringing, music, alarm, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of monitoring physiological conditions to generate an alarm signal comprising:
    monitoring location information of a health substance;
    monitoring location information and physiological information of a user;
    determining a predicted time for the user to attain a physiological condition for receiving the health substance based on the physiological information of the user;
    determining a transit time for the user to travel to a location of the health substance based on the predicted time and the location information of the user and the health substance; and
    generating an alarm signal at a time derived from the predicted and transit times to enable administration of the health substance prior to the predicted time.

2. The method of claim 1, wherein the physiological information includes environmental information associated with the user.

3. The method of claim 1, wherein the physiological information of the user includes a blood drug concentration level of the health substance in the user.

4. The method of claim 1, wherein the location information of the health substance is received from a seller of the health substance.

5. The method of claim 1, wherein the physiological condition for receiving the health substance occurs when the health substance becomes ineffective in the user.

6. The method of claim 1, wherein determining a predicted time for the user to attain a physiological condition for receiving the health substance based on the physiological information of the user further comprises:
  determining a rate at which the efficacy of the health substance is retained in the user;
  estimating a time when the concentration of the health substance will become ineffective based on the half-life of the health substance and the rate at which the efficacy of the health substance is retained in the user.

7. The method of claim 6, wherein estimating a time when the concentration of the health substance will become ineffective further comprises:
  determining the rate at which the efficacy of the health substance decays in the user based on the physiological information of the user and environmental information associated with the user; and
  adjusting the estimated time when the concentration of the health substance will become ineffective by the rate at which the health substance decays in the user.

8. A system for monitoring physiological conditions to generate an alarm signal comprising:
  at least one processor configured to:
    monitor location information of a health substance;
    monitor location information and physiological information of a user;
    determine a predicted time for the user to attain a physiological condition for receiving the health substance based on the physiological information of the user;
    determine a transit time for the user to travel to a location of the health substance based on the predicted time and the location information of the user and the health substance; and
    generate an alarm signal at a time derived from the predicted and transit times to enable administration of the health substance prior to the predicted time.

9. The system of claim 8, wherein the physiological information includes environmental information associated with the user.

10. The system of claim 8, wherein the physiological information of the user includes a blood drug concentration level of the health substance in the user.

11. The system of claim 8, wherein the location information of the health substance is received from a seller of the health substance.

12. The system of claim 8, wherein the physiological condition for receiving the health substance occurs when the health substance becomes ineffective in the user.

13. The system of claim 8, wherein determining a predicted time for the user to attain a physiological condition for receiving the health substance based on the physiological information of the user further comprises:
  determining a rate at which the efficacy of the health substance is retained in the user;
  estimating a time when the concentration of the health substance will become ineffective based on the half-life of the health substance and the rate at which the efficacy of the health substance is retained in the user.

14. The system of claim 13, wherein estimating a time when the concentration of the health substance will become ineffective further comprises:
  determining the rate at which the efficacy of the health substance decays in the user based on the physiological information of the user and environmental information associated with the user; and
  adjusting the estimated time when the concentration of the health substance will become ineffective by the rate at which the health substance decays in the user.

15. A non-transitory computer program product for monitoring physiological conditions to generate an alarm signal comprising:
  a computer readable storage medium having program instructions embodied therewith, the program instructions executable by at least one processor to cause the at least one processor to:
    monitor location information of a health substance;
    monitor location information and physiological information of a user;
    determine a predicted time for the user to attain a physiological condition for receiving the health substance based on the physiological information of the user;
    determine a transit time for the user to travel to a location of the health substance based on the predicted time and the location information of the user and the health substance; and
    generate an alarm signal at a time derived from the predicted and transit times to enable administration of the health substance prior to the predicted time.

16. The non-transitory computer program product of claim 15, wherein the physiological information includes environmental information associated with the user.

17. The non-transitory computer program product of claim 15, wherein the physiological information of the user includes a blood drug concentration level of the health substance in the user.

18. The non-transitory computer program product of claim 15, wherein the physiological condition for receiving the health substance occurs when the health substance becomes ineffective in the user.

19. The non-transitory computer program product of claim 15, wherein determining a predicted time for the user to attain a physiological condition for receiving the health substance based on the physiological information of the user further comprises:
  determining a rate at which the efficacy of the health substance is retained in the user; estimating a time when the concentration of the health substance will become ineffective based on the half-life of the health substance and the rate at which the efficacy of the health substance is retained in the user.

20. The non-transitory computer program product of claim 19, wherein estimating a time when the concentration of the health substance will become ineffective further comprises:
  determining the rate at which the efficacy of the health substance decays in the user based on the physiological information of the user and environmental information associated with the user; and
  adjusting the estimated time when the concentration of the health substance will become ineffective by the rate at which the health substance decays in the user.

* * * * *